United States Patent [19]

Christiansen

[11] Patent Number: 4,635,284
[45] Date of Patent: Jan. 6, 1987

[54] X-RAY EXAMINATION APPARATUS COMPRISING A C-SHAPED OR U-SHAPED SUPPORT FOR THE X-RAY SOURCE AND DETECTOR

[75] Inventor: Dieter H. C. Christiansen, Schönberg, Fed. Rep. of Germany

[73] Assignee: U.S. Philips Corporation, New York, N.Y.

[21] Appl. No.: 751,415

[22] Filed: Jul. 2, 1985

[30] Foreign Application Priority Data

Jul. 12, 1984 [DE] Fed. Rep. of Germany ....... 3425650

[51] Int. Cl.$^4$ .......................... H05G 1/02; A61B 6/02
[52] U.S. Cl. ...................................... 378/197; 378/193
[58] Field of Search ............................... 378/195–198, 378/193; 248/123.1

[56] References Cited

U.S. PATENT DOCUMENTS 2,831,123  4/1958  Daly ..................................... 378/198

FOREIGN PATENT DOCUMENTS 3218301  11/1983  Fed. Rep. of Germany .
2075810  11/1981  United Kingdom .

Primary Examiner—Craig E. Church
Assistant Examiner—Charles Wieland
Attorney, Agent, or Firm—Marc D. Schechter

[57] ABSTRACT

The invention relates to an X-ray examination apparatus in which the X-ray source and the X-ray detector are secured to a C-shaped or U-shaped support. This support comprises two arms which are pivotable about parallel axes and which are coupled to one another in such a way that opposite pivotal movements through equal angles are obtained. The C-shape or the U-shape of the support is then changed, so that the support can be rotated without the risk of a collision with the table top carrying the patient.

6 Claims, 7 Drawing Figures

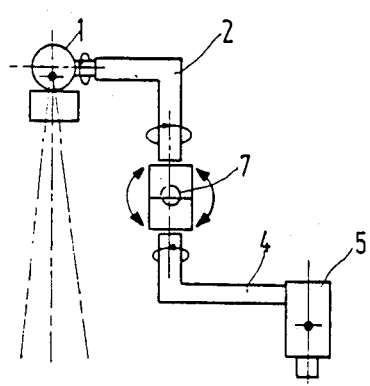
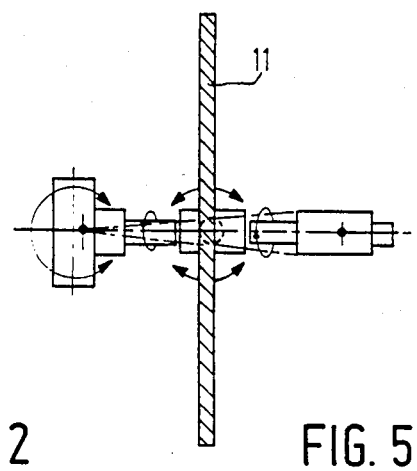
FIG. 2  FIG. 5
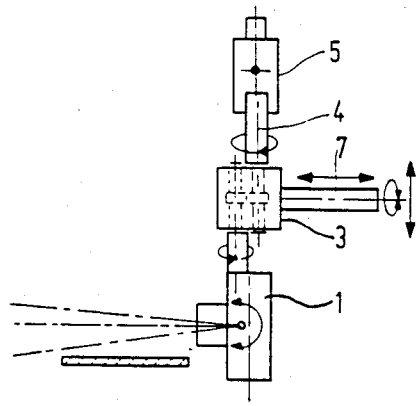
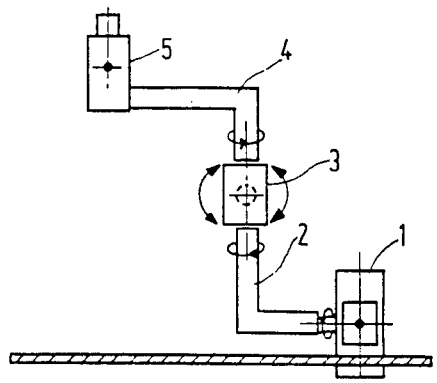
FIG. 3a  FIG. 3b
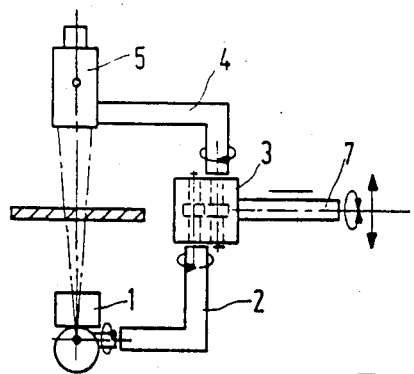
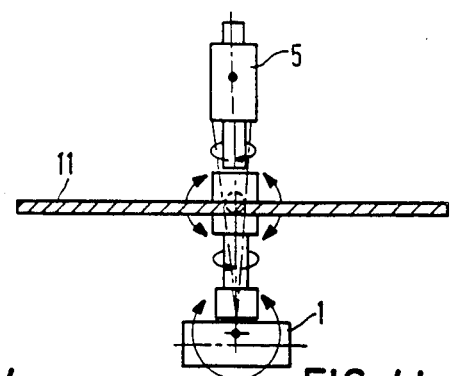
FIG. 4a  FIG. 4b

X-RAY EXAMINATION APPARATUS COMPRISING A C-SHAPED OR U-SHAPED SUPPORT FOR THE X-RAY SOURCE AND DETECTOR

BACKGROUND OF THE INVENTION

The invention relates to an X-ray examination apparatus comprising a C-shaped or U-shaped support. An X-ray source and an X-ray detector are centered relative to each other on the ends of the support. The support pivotable about an axis which is perpendicular to the connecting line between the source and the detector.

Such an apparatus is well-known. The two ends of the support carrying the X-ray source and the detector, generally an image intensifier, extend on opposite sides of a patient table from one of the longitudinal sides. When the support is rotated about a horizontal axis, the source and the detector remain centered relative to each other.

The support may be rotated until it collides with the table or the patient. For this reason a change from the under-table technique (for which the X-ray source is situated under the table) to the over-table technique (when the X-ray source is situated above the table) is only possible with such an apparatus if either the stand carrying the C-shaped or U-shaped support or the table with the patient can be moved out of the way of the other.

SUMMARY OF THE INVENTION

It is an object of the invention to provide an X-ray examination apparatus which can be switched from the under-table technique to the over-table technique without moving the entire table or the entire stand to which the C-shaped or U-shaped support is secured.

According to the invention, the support comprises two arms. One arm carries the X-ray source, and the other arm carries the detector. Both arms are pivotable about axes which extend at least substantially parallel to the connecting line between the source and the detector. The arms are coupled to one another in such a way that if one arm is pivoted in one direction the other arm is pivoted in the opposite direction with the same angular velocity.

Instead of a rigid support, the invention employs a support comprising two arms which are pivotable relative to each other. If the two arms of this support are pivoted out of the exposure position, in which the source and the detector are centered relative to one another, through an angle of 90°, about their pivotal axes, the whole support can be rotated 180°, thereby changing from the under-table technique to the over-table technique (and or vice versa) without moving the entire table top or the entire stand carrying the support.

In a preferred embodiment of the invention, the distances of the pivotal axes of the arms from the connecting line are such that when the pivotal axes are horizontal the torques on the arms exactly compensate each other. The two arms are then balanced in any position, so that they can be pivoted by the operator without the use of a motor drive.

In another preferred embodiment of the invention, the arms are coupled to each other via two gears of the same diameter. The two arms can then be balanced by an appropriate choice of the gear diameters.

In a further embodiment of the invention, the X-ray source is connected to one of the arms so as to be rotatable about an axis which is perpendicular to the pivotal axis of the arm. This embodiment enables exposures with lateral irradiation to be made using the X-ray source and another detector, for example a cassette.

BRIEF DESCRIPTION OF THE DRAWING

FIGS. 2 to 5 schematically show the arms of the apparatus in different positions.

DESCRIPTION OF THE PREFERRED EMBODIMENTS

Figure 1:
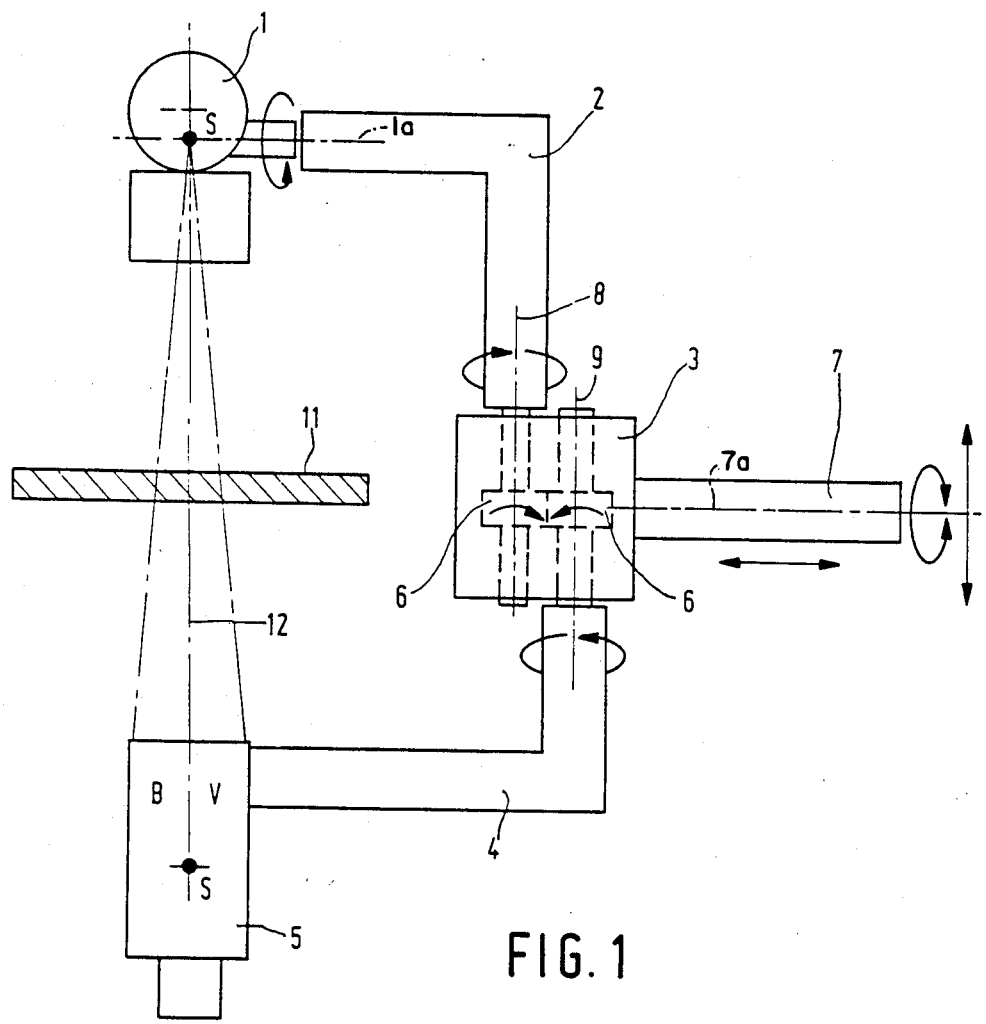
FIG. 1 schematically shows an X-ray examination apparatus according to the invention.

An X-ray source 1 is secured to a right-angled arm 2. Source 1 is mounted so as to be rotatable about a horizontal axis 1a.

The arm 2 is supported in a housing 3, which also supports a right-angled arm 4 to which an image intensifier 5 is secured. Intensifier 5 weighs less than the X-ray source 1.

In the position shown in FIG. 1 the two arms 2 and 4 together have a C-shape or U-shape to support the X-ray source 1 and the image intensifier 5 centered relative to each other. In this position, the connecting line 12 between the X-ray source 1 and the image intensifier 5 extends vertically.

The arm 2 is supported in the housing 3 so as to be pivotable about a vertical axis 8. The arm 4 is pivotable about a vertical axis 9. The axes 8 and 9 and the connecting line 12 are situated in one plane.

The two arms 2 and 4 are each rigidly connected to one of two meshing gears 6 of equal diameter accommodated in the housing 3. As is indicated by the arrows, a rotation of the arm 2 and the associated gear 6 in the counterclockwise direction results in a clockwise rotation of the other gear 6 and of the arm 4. The angles through which the arms are rotated are equal to each other.

The distances between the two pivotal axes 8 and 9 i.e. the diameters of the gears 6, are chosen such that the moments (i.e. the products of the distances of the centers of gravity S from the associated pivotal axes 8 or 9 and the masses corresponding to the loads which act on the centers of gravity S are the same. Since the two gears are always meshed, and the moments to which they are subjected are always equal but opposite, the two arms are always in balance in any position of the support.

The housing 3, in which the arms 2 and 4 are journalled, is carried by a horizontal supporting member 7 which is rotatable about its central axis 7a. Supporting member 7 is connected to the housing 3 in such a way that the moments on the central axis 7a (due to the X-ray source 1 and the image intensifier 5) exactly cancel one another. In this way, the apparatus is balanced in all angular positions and the arms 2 and 4 can be pivoted manually about their axes 8 and 9 and together about the axis 7a without any special effort.

The supporting member 7 is secured to a stand, not shown, so as to be movable in a vertical vertically. The stand is movable along the horizontal table top 11 in a longitudinal direction, i.e. perpendicular to the plane of the drawing, and in a direction transverse thereto, so that a patient on the table 11 can be irradiated from head to feet and from both sides.

When the arms 2 and 4 are each pivoted 90° out of the position shown in FIG. 1 about their respective axes 8 and 9, the support becomes S-shaped instead of C-shaped or U-shaped (see, FIG. 2). The X-ray source 1 and the image intensifier 5 are then situated beside the table top 11, enabling X-ray exposures from beside the table top 11 to be made by the X-ray source 1 and another detector, for example a cassette. Moreover, the unit can be rotated about the axis 7a, so that it occupies the position shown in FIGS. 3a and 3b if the supporting member 7 is raised and the X-ray source 1 is rotated through 90° relative to the arm 2, enabling lateral exposures to be made with the aid of detector arranged adjacent the table top 11.

If the supporting member 7 is lowered again, the X-ray source 1 is rotated back and the two arms 2 and 4 are pivoted back about their original positions about the axes 8 and 9, the position shown in FIGS. 4a and 4b is obtained. This position differs from the position shown in FIG. 1 in that the X-ray source 1 is no longer situated above the table 11 but is now underneath the table. Conversely, the image intensifier 5 is now situated above instead of underneath the table 11.

Alternatively, it is possible to set the table top 11 to a vertical position and to pivot the arms 2 and 4 through 90° (relative to the positions in FIG. 1 or 4) about the central axis 7a of the supporting member 7. This results in the position shown in FIG. 5, in which the radiation path extends horizontally. Since the moments exerted by the X-ray source 1 and the image intensifier 5 relative to the axes 8 and 9, which now extend horizontally, exactly compensate (for each other for the reasons stated above), the apparatus is also easy to operate in this position.

The apparatus parts can be latched in the desired positions in a manner which is known per se and which is not shown.

What is claimed is:

1. An X-ray examination apparatus comprising:
    a C-shaped or U-shaped support having first and second opposite ends, said support being pivotable about a first axis;
    an X-ray source arranged on the first end of the support; and
    an X-ray detector arranged on the second end of the support opposite the X-ray source, a connecting line between the source and the detector being perpendicular to the first axis;
    characterized in that:
    the support comprises first and second arms, the X-ray source being mounted on the first arm and the X-ray detector being mounted on the second arm, each arm being pivotable about a pivot axis which is substantially parallel to the connecting line; and
    the support comprises means for coupling the first arm to the second arm such that when one arm is pivoted in a first direction, the other arm is pivoted with an equal angular velocity in the opposite direction.

2. An X-ray examination apparatus as claimed in claim 1, characterized in that when the pivot axes are horizontal, their moments of the arms are equal but opposite in direction.

3. An X-ray examination apparatus as claimed in claim 2, characterized in that the coupling means comprises two gears of equal diameters.

4. An X-ray examination apparatus as claimed in claim 3, characterized in that the X-ray source is rotatably connected to the end of the first arm, the X-ray source being rotatable about an axis which is perpendicular to the pivot axis.

5. An X-ray examination apparatus as claimed in claim 1, characterized in that the coupling means comprises two gears of equal diameters.

6. An X-ray examination apparatus as claimed in claim 5, characterized in that the X-ray source is rotatably connected to the end of the first arm, the X-ray source being rotatable about an axis which is perpendicular to the pivot axis.

* * * * *